(12) United States Patent
Grimbergen et al.

(10) Patent No.: US 10,004,787 B2
(45) Date of Patent: *Jun. 26, 2018

(54) FIBRINOGEN PREPARATIONS ENRICHED IN FIBRINOGEN WITH AN EXTENDED ALPHA CHAIN

(71) Applicant: Mallinckrodt Pharma IP Trading D.A.C., Hazelwood, MO (US)

(72) Inventors: Joseph Grimbergen, Lisse (NL); Jacob Koopman, Leiderdorp (NL); Abraham Bout, Moerkapelle (NL)

(73) Assignee: Mallinckrodt Pharma IP Trading D.A.C., Dublin (IE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/614,157

(22) Filed: Jun. 5, 2017

(65) Prior Publication Data

US 2017/0266262 A1    Sep. 21, 2017

Related U.S. Application Data

(63) Continuation of application No. 14/877,354, filed on Oct. 7, 2015, now Pat. No. 9,694,054, which is a continuation of application No. 13/520,615, filed as application No. PCT/EP2011/050191 on Jan. 7, 2011, now abandoned.

(30) Foreign Application Priority Data

Jan. 8, 2010    (NL) .................................. 10150391

(51) Int. Cl.
*A61K 38/00* (2006.01)
*A61K 38/36* (2006.01)
*C07K 14/75* (2006.01)
*C12P 21/00* (2006.01)

(52) U.S. Cl.
CPC .......... *A61K 38/363* (2013.01); *C12P 21/005* (2013.01)

(58) Field of Classification Search
None
See application file for complete search history.

(56) References Cited

U.S. PATENT DOCUMENTS 5,702,715 A * 12/1997 Nikolaychik ....... A61L 24/0073
106/124.5

FOREIGN PATENT DOCUMENTS

WO    WO 03087160 A1 * 10/2003 ........... A61K 38/363

OTHER PUBLICATIONS

Fu et al. FIB420: A Normal Human Variant of Fibrinogen With Two Extended Alpha Chains. PNAS, 1994. 91:2625-2628.*

* cited by examiner

*Primary Examiner* — Christopher M Babic
*Assistant Examiner* — Kimberly A. Aron

(57) ABSTRACT

The present invention relates to fibrinogen preparations enriched in α-extended fibrinogen. Compositions comprising such preparations show improved clotting properties compared to preparations based on HMW Fib which typically contain no or only low amounts of α-extended fibrinogen. In particular, clot formation time and the clot strength of a clot made by α-extended fibrinogen are improved. In addition, plasmin-mediated degradation of α-extended fibrinogen is reduced as compared to plasma derived fibrinogen.

13 Claims, 2 Drawing Sheets

FIBRINOGEN PREPARATIONS ENRICHED IN FIBRINOGEN WITH AN EXTENDED ALPHA CHAIN

RELATED APPLICATIONS

This application is a continuation of U.S. application Ser. No. 14/877,354, filed Oct. 7, 2015, now U.S. Pat. No. 9,694,054, which is a continuation of U.S. application Ser. No. 13/520,615, filed Sep. 13, 2012 (now abandoned), which is a U.S. National Phase Application of PCT International Application PCT/EP2011/050191, filed Jan. 7, 2011, which claims priority to Netherlands (NL) Application No.: 10150391.0, filed Jan. 8, 2010. Each of the above-identified applications is incorporated herein by reference in their entirety.

FIELD OF THE INVENTION

The present invention relates to fibrinogen preparations and the use of fibrinogen preparations in medical applications. In particular, it relates to fibrinogen preparations which are enriched in fibrinogen with an extended alpha chain, to methods for producing it and to its applications.

BACKGROUND OF THE INVENTION

Fibrinogen is a soluble plasma glycoprotein which is synthesized in the human body primarily by liver parenchymal cells. It is a dimeric molecule, consisting of two pairs of three polypeptide chains designated Aα, Bβ and γ, which are connected by disulfide bridges. The three polypeptide chains are encoded by three separate genes. The predominant form (HMW fib) harbors an Aα chain which is synthesized as a 625 amino acid precursor and is present in fibrinogen found in blood plasma as a 610 amino acids polypeptide chain, the Bβ chain contains 461 and the γ chain 411 amino acids. The three polypeptides are synthesized individually from 3 mRNAs. Assembly of the three component chains (Aα, Bβ and γ) into its final form as a six-chain dimer (Aα, Bβ, γ)$_2$ occurs in the lumen of the endoplasmic reticulum (ER).

Fibrinogen circulates in blood at high concentrations (1-2 g/L) and demonstrates a high degree of heterogeneity. It is estimated that in each individual about one million different fibrinogen molecules circulate. Most of these variants, which account for just a small portion of the total fibrinogen (in most cases not more than a few percents), differ in function and structure.

Proteolysis of the carboxy-terminal part of the Aα chain results in three major circulating forms of fibrinogen having clearly different molecular weights. Fibrinogen is synthesized in the high-molecular weight form (HMW; molecular weight 340 kDa; the predominant form of Aα chains in the circulation contains 610 amino acids). The degradation of one of the Aα chains gives rise to the LMW form (MW=305 kDa); the LMW' form (270 kDa) is the variant where both Aα chains are partially degraded at the carboxy-terminus. In blood of healthy individuals, 50-70% of the fibrinogen is HMW, 20-50% is fibrinogen with one or two degraded Aα chains (de Maat and Verschuur (2005) Curr. Opin. Hematol. 12, 377). The HMW and LMW' variants show distinct differences in clotting time and fibrin polymer structure (Hasegawa N, Sasaki S. (1990) Thromb. Res. 57, 183).

Well-known variants which are the result of alternative splicing are the so-called gamma prime (γ') variant and the α-ext Fib or Fib420 variant.

The α-ext Fib or Fib420 variant, which has a molecular weight of 420 kDa, accounts for 1-3% of the total circulating fibrinogen (de Maat and Verschuur (2005) Curr. Opin. Hematol. 12, 377). The extended α-ext Fib isoform is distinguished from the conventional α-chain of fibrinogen by the presence of an additional 236 residue C-terminus globular domain due to alternative splicing. Contradictary data on the function and characteristics of Fib420 is given in literature. Based on studies with plasma derived α-ext Fib, Applegate et al., Blood (2000) 95: 2297, concluded that the polymerization and cross-linking properties of α-ext Fib are not grossly different from plasma derived HMW Fib. They conclude that the additional C-domain has no effect on coagulation and they suggest that the function of the domain may be to support integrin-mediated cell adhesion. In EP 1 495 051 it is suggested that Fib420 might be less sensitive to degradation and could have an effect on clot structure. However, no substantiation is given and there is no suggestion as to whether the effect may be an enhancement or deterioration in clot structure or strength. Mosesson et al. (Biophys. Chem. 112, 209: 2004) have studied the ultrastructure of clots that are based on umbilical cord plasma-derived α-ext Fib. They reported that the fibers of α-ext Fib clots are thinner and more branched than those based on HMW fibrinogen, but that they have the same periodicity that characterizes all fibrin fibers. The authors suggest that the likely function for the extended α-chain in α-ext Fib is to provide sites for interaction with cellular integrins.

DETAILED DESCRIPTION

The present invention relates to a fibrinogen preparation which contains at least 95% (w/w) fibrinogen and wherein at least 10% of the fibrinogen is in the form of Fib420.

In the field, Fib$_{420}$ is also referred to as 'α-ext Fib', 'fibrinogen with an extended alpha chain' or 'fibrinogen$_{420}$'. In the present context, these terms are used interchangeably. All these terms refer to a symmetrical molecule of the structure (Aα$_{ext}$, Bβ, γ), wherein both conventional fibrinogen α-chains, as found in HMW fib, have been replaced by extended chains.

In the present context, the term 'fibrinogen preparation' refers to fibrinogen in isolated form, for example to a plasma isolate or cell supernatant isolate of fibrinogen. It may also refer to a synthetic preparation of fibrinogen. A fibrinogen preparation according to the invention preferably contains at least 65% w/w, at least 70% w/w, at least 75% w/w, at least 80% w/w or at least 85% fibrinogen, based on total protein. More preferably, it is a pure preparation in which substantially no contaminants, such as other proteins, are present and it contains at least 90% w/w, at least 95% w/w, at least 96% w/w, at least 97% w/w or at least 98% fibrinogen, based on total protein. Most preferably, a fibrinogen preparation according to the invention comprises at least 99% w/w or at least 99.5% w/w fibrinogen, based on total protein. Such pure fibrinogen preparations are particularly suitable to formulate compositions which are used in medical applications, such as compositions for wound therapy and surgical repair.

According to the invention, at least 10% w/w of the fibrinogen in the preparation is in the form of Fib420. Preferably, at least 15% w/w, at least 20% w/w, at least 25% w/w or at least 30% w/w of the fibrinogen is in the form of Fib420. More preferably, at least 40% w/w, at least 50% w/w, at least 60% w/w, at least 70% w/w, at least 80% w/w or at least 90% w/w is in the form of Fib420. Most preferably, at least 95% w/w, at least 99% w/w or all of the fibrinogen is in the form of Fib420.

One advantage of the fibrinogen preparation according to the invention is that plasmin-mediated digestion of the fibrinogen preparation is slower than for plasma derived fibrinogen. Its enhanced resistance to plasmin digestion is likely to be beneficial for treatment of patients who suffer from hyperfibrinolysis which is often seen in cases of acquired coagulopathy.

Using a fibrinogen preparation according to the invention, clots are formed faster and the clots which are formed have a higher clot firmness than clots formed with plasma derived fibrinogen or HMW fibrinogen. This means that fibrin clot stability is enhanced when using the fibrinogen preparation according to the invention and that the fibrinogen preparation according to the invention is more potent than state of the art preparations. A more potent fibrinogen preparation allows for the reduction of both the amount of fluid and the amount of therapeutical protein to be administered. This is an advantage for intravenous use to treat dilutional coagulopathy. Currently, for intravenous (i.v) injection of fibrinogen to compensate for low blood clotting activity, high dosages of fibrinogen are required (~5 gram of fibrinogen per treatment). This is administered by direct injection at a dose of 70 mg/kg. As fibrinogen in general can be dissolved at a maximum concentration of 20 mg/ml, this means that about 250 ml of fluid has to be administered intravenously to in an adult. Lowering this dose by providing a more potent fibrinogen would be beneficial.

Yet another advantage is that clot formation using the fibrinogen preparation of the invention is less Factor XIII dependent than preparations of plasma derived fibrinogen or HMW fibrinogen. The strength of a clot made in buffer by alpha-extended Fib (so in the absence of Factor XIII) is higher than for plasma-derived fibrinogen which will contain some Factor XIII No Factor XIII is required to form firm clots. Therefore, in one embodiment, the fibrinogen preparation according to the invention is free of Factor XIII.

Clotting time (CT), clot formation time (CFT) and clot firmness of α-ext rhFib and plasma derived fibrinogen can be measured using ROTEM analysis. ROTEM® (Pentapharm GmbH, Munich, Germany) stands for ROtation ThromboElastoMetry. The technique utilizes a rotating axis submerged in a (blood) sample in a disposable cuvette. Changes in elasticity under different clotting conditions result in a change in the rotation of the axis, which is visualized in a thromboelastogram, reflecting mechanical clot parameters (see e.g. Luddington R. J. (2005) Clin Lab Haematol. 2005 27(2):81).

In a ROTEM® system test under similar conditions, a fibrinogen preparation according to the invention typically performs at least as good or better than a fibrinogen preparation or composition in which the fibrinogen variant distribution resembles the variant distribution in human plasma, viz. less than 5% w/w of the fibrinogen is of the Fib420 type. This is for example the case for fibrinogen concentrates which are based on plasma-derived fibrinogen. Such concentrates are commercially available. In particular, its clot formation time will be less than the clot formation time of a fibrinogen preparation in which less than 5% w/w of the fibrinogen is of the Fib420 type. Preferably, the clot formation time of a fibrinogen preparation according to the invention is maximally 80%, maximally 60%, maximally 50%, maximally 40%, maximally 30%, maximally 20%, maximally 10% of the clot formation time of a fibrinogen preparation in which less than 5% w/w of the fibrinogen is of the Fib420 type, such as plasma-derived fibrinogen preparations. The ROTEM experiments with α-ext rhFib presented in the Examples indicate that a fibrinogen preparation according to the invention has a clot formation time (CFT) which is less than the CFT of purified plasma derived fibrinogen produced for intravenous applications.

In another aspect, the invention relates to a composition comprising a fibrinogen preparation according to the invention. In addition to the fibrinogen, the composition may comprise an activator, such as thrombin or a thrombin-like protein, such as reptilase. It may also comprise excipients which are suitable for use in an injectable preparation. The preparation may be in dry form and subsequently reconstituted, with e.g. buffered saline, and the like, or it may be in liquid form, either as a suspension or solution. Suitable excipient materials may include solvents and co-solvents, such as ethanol, glycerin, PEGs, oils, and the like; solubilizing, wetting, suspending, emulsifying or thickening agents, such as carboxymethylcellulose, hydrolyzed gelatin, pluronics, polysorbates, and the like; chelating agents, such as calcium EDTA, DTPA, and the like; antioxidants and reducing agents, such as BHT, ascorbic acid, sodium metabisulphite, and the like; antimicrobial preservatives, such as benzyl alcohol, phenol, parabens, and the like; buffers and pH adjusting agents, such as tromethamine, sodium phosphate, sodium acetate, sodium hydroxide, and the like; bulking agents, protectants, and tonicity adjustors, such as alanine, albumin, dextran, lactose, sorbitol, sodium chloride, histidine, and the like; special additives, such as simethicone as anti-foaming agent, trehalose for reduction of protein aggregation.

The composition may be used in any application in which plasma-derived or recombinant fibrinogen is used. The main applications are hemostasis and to seal tissue. In one embodiment of the invention, the composition is a pharmaceutical composition. The pharmaceutical composition comprises a fibrinogen preparation according to the invention and a pharmaceutically acceptable carrier. "Pharmaceutically acceptable carrier" refers to a vehicle, auxiliary agent, adjuvant, diluent, excipient or carrier with which the fibrinogen preparation of the invention is administered. Examples of pharmaceutically acceptable carriers include, without limitation, water, buffered saline, ethanol, polyol (for example, glycerol, propylene glycol, liquid polyethylene glycol and the like), dimethyl sulfoxide (DMSO), oils, detergents, suspending agents or suitable mixtures thereof. Suitable pharmaceutically acceptable carriers and formulations are described in Remington's Pharmaceutical Sciences, 19th Ed. (Mack Publishing Co., Easton, 1995) and "Remington: The Science And Practice Of Pharmacy" by Alfonso R. Gennaro (Lippincott Williams & Wilkins, 2005).

The pharmaceutical composition may be applied topically and may include carriers which are water-soluble, water-absorbent, water-insoluble or water-swellable. Suitable materials include saccharides such as mono-and di-saccharides, including lactose, mannitol and trehalose, or dextran and dextran polymers, like e.g. Sephadex, which are available in different particle sizes, starches, pullulan derivatives, hyaluronic acid esters, and the like. Cellulose products such as microcrystalline cellulose (Avicel range), methylcellulose, carboxymethyl cellulose, microtine cellulose or hydroxy propyl cellulose, and other materials such as cross-linked polyvinyl pyrrolidone (PVP), may be used singly or in admixture. Also, suitable carriers include polyethylene glycol (PEG), preferably having a molecular weight of about 1000; polyvinylpyrrolidone (PVP), preferably having an average molecular weight of about 50,000; poly(acrylic acid), PVA, poly(methylvinylether co-maleic anhydride), poly(ethyleneoxide), and dextran, typically having an average molecular weight of about 40,000.

Tablet disintegrants may be included. These materials will absorb moisture from the wound, expand rapidly and thereby enhance the wettability of the hemostatic components of the powder blend. Suitable examples include sodium starch glycolate (Explotab® or Primojel®) which has an average particle size in the range of 35-55 µm. About 25% of the glucose units are carboxymethylated; cross-linked polyvinyl pyrrolidone (Polyplasdone®); alginates and alginic acid; cross-linked sodium carboxymethylcellulose (Ac-Di-Sol). Gums and gelling agents that can be used include, for example, tragacanth, karaya gum, soluble starch, gelatin, pectin, guar gum and gellan gum.

A particularly preferred additive is Emdex®, i.e. a hydrated form of dextrates (spray crystallized dextrose containing small amounts of starch oligosaccharides). It is a highly refined product composed of white, free-flowing, spray-crystallized macroporous spheres with a median particle size of 190-220 µm.

A most preferred additive is NON-PAREIL SEEDS®: (Sugar Spheres). These are used in multiple drug units for improved content uniformity, consistent and controlled drug release and high drug stability, size ranges from 200 to 2000 mm.

The pharmaceutically acceptable carrier may comprise an effervescent couple. The gas produced following an effervescent reaction can expand the fibrin sealant into a 'foam' and/or increase wettability of the powders comprising the fibrin sealant. As the powders are applied to a wound, the effervescent components dissolve, react and liberate, say, carbon dioxide, thereby increasing the wettability of the hemostatic components and thus enhancing time to clot formation. The fibrin sealant will appear as a stable foam once fully reacted and the clot has formed.

The effervescent couple typically comprises citric acid or sodium hydrogen citrate and sodium bicarbonate, but other physiologically acceptable acid/alkaline or alkaline earth metal carbonate mixtures may be used, for example tartaric, adipic, fumaric or malic acids, and sodium, potassium or calcium (bi)carbonates or sodium glycine carbonate.

In general it has been found that preferred taste characteristics are exhibited when the relative proportions of the components of the effervescent couple on a chemical molecular equivalent basis are in the range of 4:3 to 1:3, more preferably about 2:3, expressed as the ratio of molecular equivalent of the acidic component to the basic component. In terms of a preferred combination of citric acid and sodium bicarbonate these values represent on a weight basis, a range from 1:1 to 0.3:1, preferably 0.5:1 expressed as the ratio of acidic to basic component.

The pharmaceutical composition according to the invention is suitable for facilitating tissue adherence, improving wound healing or for intravenous administration.

In one embodiment, the pharmaceutical composition according to the invention is a fibrin sealant. The fibrin sealant according to the invention typically comprises thrombin. The sealant may be in any convenient form, be it dry or liquid. A suitable example of a dry sealant in which the fibrinogen preparation according to the invention may be used is Fibrocaps® powder sealant, which is described in WO97/44015 and which is based on micro-particles of fibrinogen and thrombin. The separate components are prepared by spray-drying, fibrinogen with trehalose and thrombin with trehalose. Each powder component has a predominant particle size of approximately up to 50 µm in diameter. The Fibrocaps® fibrin sealant, which is a blend of these components, has been demonstrated to be an easy-to-use, stable and efficacious topical haemostat. The product can be used immediately, without reconstitution and is useful in wound therapy, in surgical repair and as an extravascular stent. On contact with aqueous fluid such as blood, the exposed active thrombin converts the exposed fibrinogen into insoluble fibrin polymers. The fibrinogen preparation according to the invention would give further improved blood clotting properties.

The composition of the invention may be applied to wounds, sutures, incisions and other openings where bleeding may occur. A wound includes damage to any tissue in a living organism. The tissue may be an internal (e.g. organ) or external tissue (e.g. eye or skin), and may be a hard tissue (e.g. bone) or a soft tissue (e.g, liver or spleen). The wound may have been caused by any agent, including infection, surgical intervention, burn or trauma. The composition of the invention may be used for surgical interventions such as in the gastrointestinal system, e.g. the oesophagus, stomach, small intestine, large intestine, rectum, on parenchymal organs such as the liver, pancreas, spleen, lungs, kidney, adrenal glands, lymph and thyroid glands; surgical interventions in the ear, nose and throat area (ENT) including dental surgery, cardiovascular surgery, aesthetic surgery, neurological surgery, lymphatic, biliary, and cerebrospinal (C SF) fistulae, air leakages during thoracic and pulmonary surgery, thoracic surgery including surgery of the trachea, bronchi and lungs, gynaecological, vascular, urological, bone (e.g. spongiosa resection), and emergency surgery.

As an extravascular stent or support, the composition of the invention may be applied to the outside of a segment or the whole of a vein graft. A suitable extravascular stent composition is a composition of a fibrinogen preparation according to the invention and thrombin. The composition may be in any suitable form, be it liquid or dry. In one embodiment, a dry powder composition, for instance one as described above, is used as an extravascular stent. The dry powder composition polymerizes in the limited amounts of bodily fluids which are naturally present at the outside of the vessel wall, thus forming an extravascular stent.

A vein coated with an extravascular stent composition according to the present invention is also part of the invention. The vein may be any kind of vein which needs to be protected from overextension or which needs support, for instance a varicose vein. In a preferred embodiment, the vein is a venous graft. In one embodiment, the composition is applied before the venous graft is introduced in the human or animal body. In another embodiment, the composition is applied after the venous graft has been introduced in the human or animal body.

In yet another aspect, the present invention relates to the use of a fibrinogen preparation according to the invention as a medicament. It can be used for the preparation of a medicament for the treatment of acute bleeding episodes, hyperfibrinolysis, fibrinogen deficiency, be it acquired or congenital, or other bleeding disorders.

In one embodiment, a composition according to the invention is used in a method for reducing bleeding at a hemorrhaging site. Preferably, a hemostatically effective amount of the composition according to the invention is used. When used as a topical haemostat, a time to hemostasis (TTH) of about 10 minutes or less, about 5 minutes or less, or about 3 minutes or less may be achieved. In the present context, TTH is the time it takes to stop a bleeding. If a pressure sheet is used, measurement of TTH typically starts when the pressure sheet is applied to the bleeding site and runs until bleeding stops by visualization of the dressing and/or no bleeding through or around the dressing is observed.

In yet another aspect, the present invention relates to a method for preparing a fibrinogen preparation according to the invention. Such preparation may be prepared in any suitable way, using techniques available in the art. In order to produce α-ext Fib in an economically feasible way, high expression levels of intact, functional fibrinogen are required and therefore recombinant production is preferred. In the context of the present invention, fibrinogen or a fibrinogen chain is 'in intact form' when the amino acid sequence contains all the amino acids which were encoded for by the nucleotide sequence, optionally without the amino acids which are removed during normal cell (secretion) processing. Therefore, alpha-ext chains having 866 or 847 amino acids are examples of an alpha chain in intact form.

Recombinant production of fibrinogen has many advantages over the use of plasma derived materials. These include its preferred safety profile, the possibility to make pure homogeneous preparations of variants free of any other blood born contaminants and the unlimited supply. In addition, for specific applications (e.g. use of fibrinogen as an intravenous hemostat) proper post-translational modifications (e.g. glycosylation) are required. Therefore, expression in eukaryotic, in particular mammalian systems, more particular in human systems, is preferred.

In a preferred embodiment, a fibrinogen preparation according to the invention is prepared by a method which comprises the steps of:

providing an expression vector comprising a nucleic acid sequence, which nucleic acid sequence encodes an alpha extended polypeptide chain of fibrinogen;

transforming a eukaryotic cell with the expression vector;

maintaining the transformed eukaryotic cell under such conditions which allow for the expression of the nucleic acid sequence encoding the alpha extended polypeptide chain of fibrinogen.

Expression vectors for eukaryotic hosts are known in the art and any of the vectors conventionally used for expression in eukaryotic cells may be used. An expression vector typically contains a promoter operably linked to the nucleic acid sequence to be expressed and ribosome binding sites, polyadenylation signals, transcription termination sequences, upstream regulatory domains and enhancers. In one embodiment, an expression vector for expression in mammalian cells, such as for CHO or PER.C6® cells is used. Such vectors are known in the art and suitable examples include pcDNA3.1 plasmids, GATEWAY (Invitrogen), pCMV/Bsd (Invitrogen), pFN vectors (Promega) and numerous other vector systems. The PER.C6® cells are as deposited under European Collection of Animal Cell Cultures (ECACC) No. 96022940.

In the present context, 'an alpha extended polypeptide chain of fibrinogen' may refer to a fibrinogen alpha chain of 866 amino acids with a signal sequence or to one without a signal sequence and to any variants thereof which have arisen through genetic polymorphisms or differences in glycosylation and phosphorylation. A suitable example of an alpha extended chain amino acid sequence is given in SEQ ID No. 1. The terms 'alpha chain' and 'Aα chain' are used interchangeably in the context of the present invention.

The skilled person will understand that the eukaryotic cell must also contain nucleic acid sequences which encode the beta and gamma chain of fibrinogen to be able to produce a fibrinogen molecule. Recombinant production of fibrinogen from alpha, beta and gamma chains have been described before, see for instance PCT/EP2009/058754, U.S. Pat. No. 6,037,457 or WO 95/023868.

In the context of the present invention, the terms 'beta chain' and 'Bβ chain' are used interchangeably. They may refer to both wild type and variants of the beta chain, with or without signal sequence. A suitable example of a fibrinogen beta chain amino acid sequence is given in SEQ ID No. 2.

In the context of the present invention, the term 'gamma chain' and 'γ chain' are used interchangeably. They may refer to both wild type and variants of the gamma chain, with or without signal sequence. Suitable examples of a fibrinogen gamma chain amino acid sequence are given in SEQ ID No. 3 and 4.

Preferably, the nucleic acid sequences encoding a fibrinogen chain are optimized. An optimized nucleic acid sequence allows for the efficient expression of recombinant fibrinogen in intact form. Preferably, they are optimized for expression in a eukaryotic cell culture system, such as for expression in a COS cell, BHK cell, NS0 cell, Sp2/0 cell, CHO cell, a PER.C6 cell, a HEK293 cell or insect cell culture system. More preferably, they are optimized for expression in a mammalian cell culture system. Most preferably, the nucleic acid sequences are optimized for expression in a human cell culture system, such as for a PER.C6 cell or a HEK293 cell culture system. The nucleotide sequence which is optimized may be DNA or RNA. Preferably, it is cDNA.

An optimized nucleotide sequence encoding a fibrinogen alpha extended, beta or gamma chain shows at least 70% identity to its respective non-optimized counterpart. In one embodiment, an optimized nucleotide sequence encoding a fibrinogen α-ext Fib, Bβ and γ chain shows 70-80% identity to its respective non-optimized sequences. Preferably, the optimized nucleotide sequences encoding a fibrinogen alpha extended, beta or gamma chain contain no cis-acting sites, such as splice sites and poly(A) signals.

An optimized nucleotide sequence which is used in the method according to the invention and which encodes a fibrinogen alpha extended chain contains no 39 basepair direct repeat sequences which are normally present in the gene encoding the alpha chain of human fibrinogen. The repeating sequence must be changed without changing the encoded protein sequence.

In a preferred embodiment, an optimised nucleotide sequence according to SEQ ID NO. 5 or the part of this sequence without the signal (nucleotides 60-2598) is used for expressing the alpha extended chain.

In another preferred embodiment, an optimised nucleotide sequence according to SEQ ID NO. 6 or the part of this sequence without the signal sequence (nucleotides 93-1473) is used for expressing the beta chain.

In another preferred embodiment, an optimised nucleotide sequence according to SEQ ID NO. 7 or 8 or the part of these sequences without a signal sequence (nucleotides 51-1311 of SEQ ID NO. 7 and nucleotides 51-1359 of SEQ ID NO. 8) is used for expressing the gamma chain.

Nucleic acid sequences according to the invention may be encoding any type of fibrinogen chains. Preferably they are encoding mammalian fibrinogen chains, more preferably they are encoding primate fibrinogen chains, most preferably they are encoding human fibrinogen chains. Also combinations are possible, such as for example one or two mammalian fibrinogen chains combined with two or one rodent fibrinogen chains. Recombinant expression according to the method of the present invention allows for expression levels of Fib420 which are similar to those of recombinant HMW Fib.

BRIEF DESCRIPTION OF THE DRAWINGS

FIG. 2 includes Panels A through F, as follows:

Panel A: Plasma derived fibrinogen (Haemocomplettan, CSL Behring, Marburg, Germany) in buffer;

Panel B: PER.C6 derived recombinant HMW fibrinogen (α-625) in buffer;

Panel C: PER.C6 derived rhFib-ext fibrinogen (α-847) in buffer;

Panel D: Plasma derived fibrinogen (Haemocomplettan, CSL Behring, Marburg, Germany) mixed with plasma;

Panel E: PER.C6 derived recombinant HMW fibrinogen (α-625) mixed with plasma;

Panel F: PER.C6 derived rhFib-ext fibrinogen (α-847) mixed with plasma.

Figure 3:
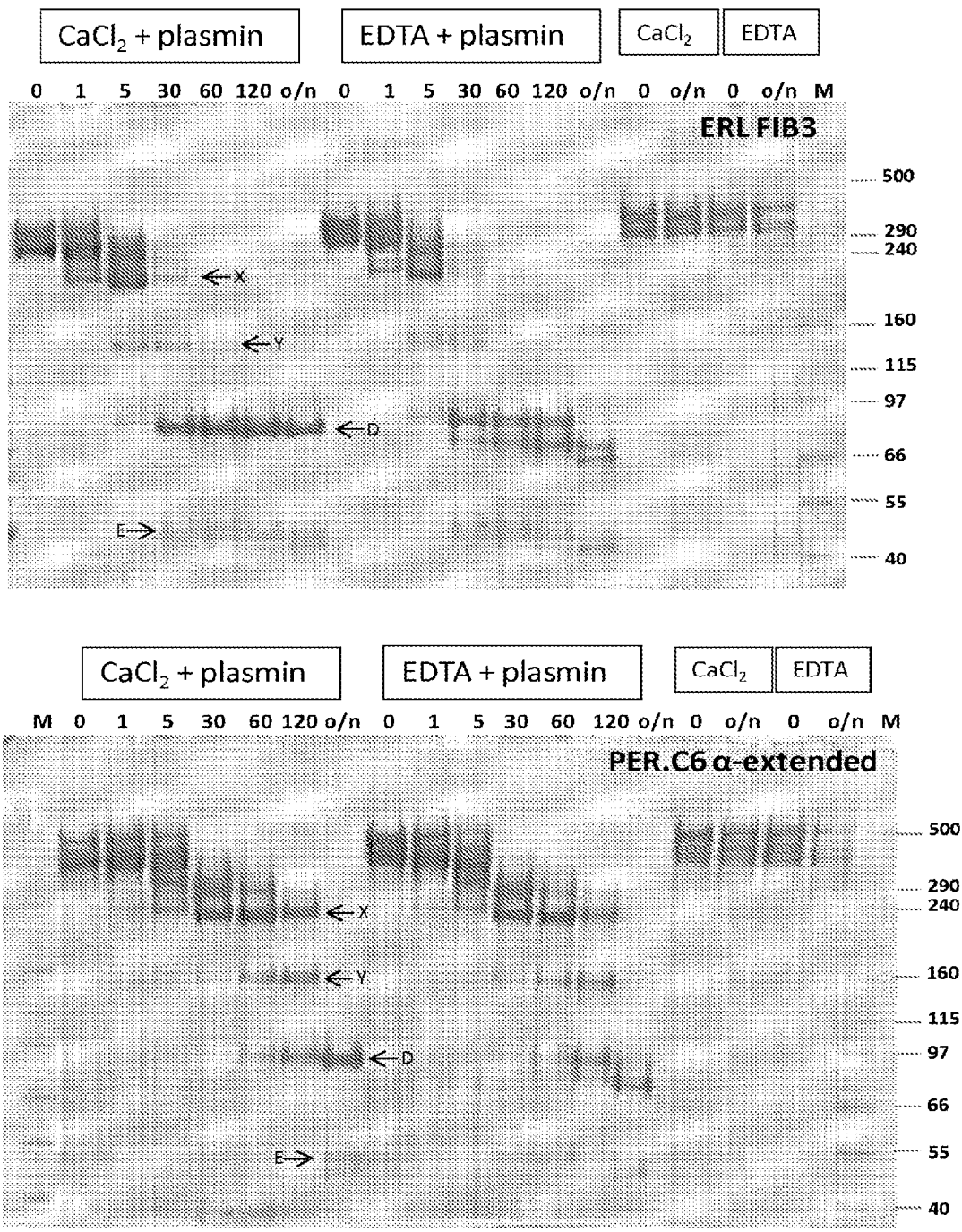

FIG. 3 The picture shows a Coomassie stained protein gel loaded with material from plasmin degraded plasma derived material (ERL FIB3; upper panel, and α-ext Fib (lower panel). The conditions are indicated on top of the gel; the time of incubation (0, 1, 5, 30, 60 and 120 minutes and o/n (overnight)) is shown as well. At the right of the gel the MW marker is displayed.

EXAMPLES

Example 1

Preparation of Optimized cDNA Constructs cDNAs coding for human fibrinogen polypeptide chains of α-ext Fib (Fib420), Bβ and γ, were synthesized in codon optimized format by GeneArt (Regensburg, Germany): (i) cis-acting sites (splice sites, poly(A) signals) were removed; (ii) repeat sequence of Aα chain was modified; (iii) GC content was increased for prolonged mRNA half life; (iv) Codon usage was adapted to CHO (codon adaption index—CAI->0.95).

The codon optimized cDNAs for α-ext Fib (SEQ ID NO.5), Bβ (SEQ ID No. 6), and γ (SEQ ID NO. 6) chain were subcloned in pcDNA3.1 deriviates. Aα-extended (Fib420) in pcDNA3.1(+) neo, Bβ chains in pcDNA3.1(+) hygro and γ chain in pcDNA3.1(-)hygro (Invitrogen, Carlsbad, USA).

Example 2

PER.C6 Cell Lines Expressing Recombinant Human α-ext Fib

The generation of PER.C6 cell lines producing recombinant human fibrinogen is similar as described before in PCT/EP2009/058754. In summary, cells were cultured in suspension in MAb medium and transfected using the AMAXA nucleofection device (program A-27) and using Nucleofector kit T with three vectors encoding the three different chains of the human fibrinogen protein (Aα-ext, Bβ and γ chain) and containing the optimized cDNA chains (SEQ ID no.5, SEQ ID no. 6, and SEQ ID no.7, respectively).

After transfection and plating in 96-well plates, 325 clones were transferred and screened in 48-well plates. At the end of the expansion path, 24 clones were transferred to shaker flasks, of which 8 were selected for stability and expression analysis in continued batch culture testing.

Figure 1:
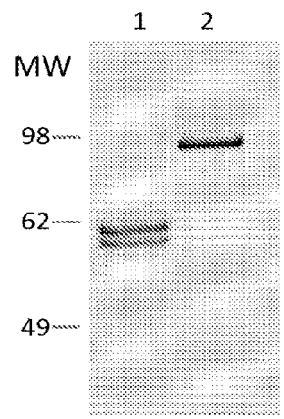
FIG. 1 Western blot analysis. Lane 1 is a control containing plasma derived wild-type fibrinogen (FIB3, Enzyme Research Laboratories). Lane 2 contains culture supernatant of clone W115, a PER.C6 clones expressing α-ext rhFib. The molecular weight marker (MW) is indicated at the left.

Yields in batch culture were similar to yields obtained with cell lines that express the Aα-chain in 610 or 625 amino acid format, indicating that the extension of the Aα-chain does not impair expression levels. This was not expected on forehand, as plasma derived fibrinogen only contains 1-3% of extended Aα-chain as compared to 610/625 Aα-chain containing fibrinogen. Protein analysis using SDS-PAGE and Western blotting analysis indicate that the recombinant fibrinogen is produced in intact format, with the α-chain having the expected size (FIG. 1).

Example 3

Purification of α-Extended Fibrinogen from PER.C6 Cell-Culture Medium

Recombinant human α-extended fibrinogen was purified from cell culture supernatant according to standard methods. Briefly, $(NH_4)_2SO_4$ was added to the culture supernatant to 40% saturation and the precipitate was collected by centrifugation. Subsequently, the precipitate was dissolved in TMAE loading buffer (5 mM Tris-HCl pH 8.5, 0.01% Tween-20) followed by dialysis to the same buffer. The protein solution was then loaded on a Fractogel EMD TMAE (m) 40-90 μm (3 ml) (Merck KGaA, Darmstadt, Germany) Ion Exchange Column. Recombinant human α-extended fibrinogen was subsequently eluted using a continuous salt gradient of 0-1 M NaCl in 20 column volumes.

Recombinant human fibrinogen in the peak fractions was precipitated again by adding $(NH_4)_2SO_4$ to 40% saturation and collected by centrifugation. Finally the material was dissolved in TBS (50 mM Tris-HCl, pH7.4, 100 mM NaCl) and dialysed against TBS to remove any remaining $(NH_4)_{SO4}$.

Example 4

ROTEM Analysis

Clotting time (CT), clot formation time (CFT) and clot firmness of α-ext rhFib and plasma derived fibrinogen were measured using ROTEM analysis. ROTEM® (Pentapharm GmbH, Munich, Germany) stands for ROtation ThromboElastoMetry. The technique utilizes a rotating axis submerged in a (blood) sample in a disposable cuvette. Changes in elasticity under different clotting conditions result in a change in the rotation of the axis, which is visualized in a thromboelastogram, reflecting mechanical clot parameters (see e.g. Luddington R. J. (2005) Clin Lab Haematol. 2005 27(2):81).

Pooled normal (citrate) plasma was mixed 1:1 with plasma-derived fibrinogen (Haemocomplettan, CSL Behring GmbH, Marburg, Germany) or PER.C6 fibrinogen (HMW rhFib or α-ext rhFib) all at 2 mg/ml in TBST (TBS+0.001% Tween-20). Also the fibrinogen preparations (at 2 mg/ml in TBST) were used directly. $CaCl_2$ was added to a final concentration of 17 mM (measurement in plasma) or 1.7 mM (measurement in buffer). To start clotting, α-thrombin was added to a final concentration of 1 IU/ml.

Figure 2:
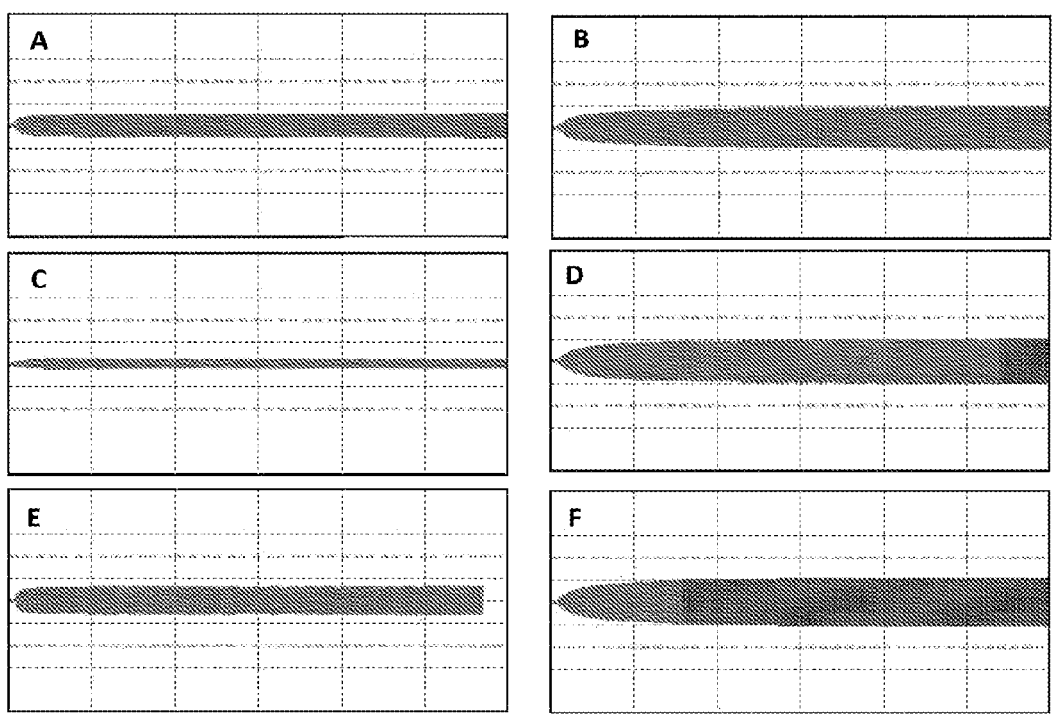
FIG. 2 ROTEM analysis. Clotting time, clot formation time and clot firmness were determined by ROTEM analysis. The left panels display the fibrinogen preparations in buffer, the right panels display plasma mixed 1:1 with the fibrinogen preparations.

ROTEM® analysis graphs for the fibrinogen preparations in buffer or mixed 1:1 with plasma are shown in FIG. 2. A10, A20, CFT and MCF values (mm) are shown in Table 1. A10 and A20 reflect the firmness of the clot at 10 and 20 minutes post α-thrombin addition. CFT reflects the time from initiation of clotting until a clot firmness of 20 mm is detected. MCF reflects maximum clot firmness.

The results indicate that clotting of α-ext rhFib in buffer results in a stronger clot (A10=12 mm) than what is observed for HMW rhFib (A10=4 mm). Plasma derived fibrinogen has an A10 of 15 mm; this stronger clot formation in buffer can be explained by the activity of co-purified blood derived FXIII which will (partially) cross-link the fibrin monomers. In purified recombinant fibrinogen, no FXIII is present and hence no cross-linking can occur. This can be compensated for by running the experiment in diluted plasma (which contains FXIII). In this case, stronger clots are formed. Interestingly, in this situation, α-ext rhFib forms a stronger clot and forms it faster than HMW rhFib or plasma derived Fib, with A20 values of 21, 18 and 17 mm, resp.

TABLE 1

| Sample | CT (sec) | A10 (mm) | A20 (mm) | MCF (mm) | CFT (sec) |
|---|---|---|---|---|---|
| Plasma-derived fbg in buffer | 47 | 10 | 10 | 10 | — |
| Plasma-derived fbg in plasma | 50 | 15 | 17 | 18 | 4696 |
| PER.C6 α-625 fbg in buffer | 70 | 4 | 4 | 4 | — |
| PER.C6 α-625 fbg in plasma | 61 | 17 | 18 | 20 | 3368 |
| PER.C6 α-847 fbg in buffer | 49 | 12 | 12 | 12 | — |
| PER.C6 α-847 fbg in plasma | 62 | 18 | 21 | 21 | 950 |

Example 5

Plasmin Digestion of α-ext rhFib and Plasma Derived Fibrinogen

Fibrinogenolysis of purified recombinant human α-ext rhFib was tested by incubation with plasmin. Briefly, fibrinogen was diluted in TBST (50 mM Tris-HCl, pH7.4, 100 mM NaCl, 0.01% Tween-20), CaCl2 or EDTA was added (5 mM final concentration) and plasmin was added (10 nM final concentration), followed by an incubation at 37° C. At several points in time samples were taken and mixed immediately with SDS-PAGE sample buffer (NuPAGE LDS sample buffer, Invitrogen, cat# NP0007). Samples were then subjected to size separation on a non-reduced SDS-PAGE gel (NuPAGE 3-8% Tris-Acetate, Invitrogen, cat# WG1602). Protein was visualized by Coomassie staining (SimplyBlue SafeStain, Invitrogen, cat# LC6060).

The results, as shown in FIG. 3, indicate that the plasmin mediated digestion of α-ext rhFib is significantly slower than for plasma derived fibrinogen. For example, in the presence of Ca2+, after 60 minutes all of the plasma derived fibrinogen is degraded down to fragment D and E species. For α-ext rhFib this takes more than 120 minutes and only the overnight incubation shows substantial amounts of fragment E generation, which are already present in the digest of the plasma derived fibrinogen after 30 minutes.

What is claimed is:

1. A pharmaceutical human fibrinogen preparation in dry form comprising at least 95% (w/w) fibrinogen based on total protein and wherein at least 10% (w/w) of the fibrinogen is in the form of fibrinogen with an extended alpha polypeptide chain(Fib420), wherein the Fib420 is prepared by a method comprising the step of:
   a) providing an expression vector comprising a nucleotide sequence encoding the alpha extended polypeptide chain of Fib420;
   b) transforming a mammalian cell with the expression vector; and
   c) maintaining the transformed mammalian cell under such conditions which allow for the expression of the nucleotide sequence encoding the alpha extended polypeptide chain of Fib420,
   wherein the nucleotide sequence comprises SEQ ID NO. 5 or nucleotides 69-2598 of SEQ ID NO. 5.

2. The pharmaceutical human fibrinogen preparation of claim 1, which is free of Factor XIII.

3. A pharmaceutical composition comprising the human fibrinogen preparation of claim 1 and a pharmaceutically acceptable carrier, diluents or excipient.

4. The pharmaceutical composition of claim 3, wherein the composition is suitable for facilitating tissue adherence, improving wound healing or for intravenous administration.

5. The pharmaceutical composition of claim 3, wherein the pharmaceutical composition is a fibrin sealant or a topical haemostat.

6. The pharmaceutical composition of claim 3 which further comprises thrombin.

7. The pharmaceutical composition of claim 3 in dry form.

8. The pharmaceutical human fibrinogen preparation of claim 1 for use as a medicament.

9. The pharmaceutical human fibrinogen preparation according to claim 1 for use in a method for treating acute bleeding episodes, hyperfibrinolysis, fibrinogen deficiency or other bleeding disorders.

10. A method for preparing a fibrinogen preparation comprising fibrinogen with an extended alpha polypeptide chain (Fib420), wherein the method comprises:
   a) providing an expression vector comprising a nucleotide sequence encoding the alpha extended polypeptide chain of Fib420;
   b) transforming a mammalian cell with the expression vector; and
   c) maintaining the transformed mammalian cell under such conditions which allow for the expression of the nucleotide sequence encoding the alpha extended polypeptide chain of Fib420,
   wherein the nucleotide sequence comprises SEQ ID NO. 5 or nucleotides 69-2598 of SEQ ID NO. 5.

11. The method of claim 10, wherein the mammalian cell is a human cell.

12. The method of claim 10, wherein the mammalian cell is a PER.C6 cell.

13. The method of claim 10, wherein fibrinogen preparation is free of Factor XIII.

\* \* \* \* \*

SEQUENCE LISTING

<160> NUMBER OF SEQ ID NOS: 8

<210> SEQ ID NO 1
<211> LENGTH: 866
<212> TYPE: PRT
<213> ORGANISM: Homo sapiens

<400> SEQUENCE: 1

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
```

```
                130                 135                 140
Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
                180                 185                 190

Asp Leu Lys Asp Tyr Glu Asp Gln Gln Lys Gln Leu Glu Gln Val Ile
                195                 200                 205

Ala Lys Asp Leu Leu Pro Ser Arg Asp Arg Gln His Leu Pro Leu Ile
                210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
                275                 280                 285

Pro Ser Ser Ala Gly Ser Trp Asn Ser Gly Ser Ser Gly Pro Gly Ser
                290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
                355                 360                 365

Ser Ala Gly His Trp Thr Ser Glu Ser Ser Val Ser Gly Ser Thr Gly
                370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
                435                 440                 445

Val Thr Ser Gly Ser Thr Thr Thr Arg Arg Ser Cys Ser Lys Thr
                450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
                500                 505                 510

His Pro Asp Glu Ala Ala Phe Phe Asp Thr Ala Ser Thr Gly Lys Thr
                515                 520                 525

Phe Pro Gly Phe Phe Ser Pro Met Leu Gly Glu Phe Val Ser Glu Thr
                530                 535                 540

Glu Ser Arg Gly Ser Glu Ser Gly Ile Phe Thr Asn Thr Lys Glu Ser
545                 550                 555                 560
```

Ser Ser His His Pro Gly Ile Ala Glu Phe Pro Ser Arg Gly Lys Ser
            565                 570                 575

Ser Ser Tyr Ser Lys Gln Phe Thr Ser Thr Ser Tyr Asn Arg Gly
        580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
            645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
            675                 680                 685

Trp Gln Asp Tyr Lys Arg Gly Phe Gly Ser Leu Asn Asp Glu Gly Glu
        690                 695                 700

Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
            725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
            755                 760                 765

Gly Ser Val Glu Glu Gly Ala Glu Tyr Thr Ser His Asn Asn Met Gln
770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
            805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
            835                 840                 845

Ala Asp Tyr Ser Leu Arg Ala Val Arg Met Lys Ile Arg Pro Leu Val
    850                 855                 860

Thr Gln
865

<210> SEQ ID NO 2
<211> LENGTH: 491
<212> TYPE: PRT
<213> ORGANISM: Homo sapiens

<400> SEQUENCE: 2

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro

-continued

```
            50                  55                  60
Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
                100                 105                 110

Gln Glu Ala Leu Leu Gln Gln Glu Arg Pro Ile Arg Asn Ser Val Asp
                115                 120                 125

Glu Leu Asn Asn Asn Val Glu Ala Val Ser Gln Thr Ser Ser Ser Ser
                130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
                180                 185                 190

Thr Asn Leu Arg Val Leu Arg Ser Ile Leu Glu Asn Leu Arg Ser Lys
                195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
                260                 265                 270

Asn Thr Glu Asn Gly Gly Trp Thr Val Ile Gln Asn Arg Gln Asp Gly
                275                 280                 285

Ser Val Asp Phe Gly Arg Lys Trp Asp Pro Tyr Lys Gln Gly Phe Gly
                290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
                340                 345                 350

Lys Ala His Tyr Gly Gly Phe Thr Val Gln Asn Glu Ala Asn Lys Tyr
                355                 360                 365

Gln Ile Ser Val Asn Lys Tyr Arg Gly Thr Ala Gly Asn Ala Leu Met
                370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
                420                 425                 430

Trp Tyr Asn Arg Cys His Ala Ala Asn Pro Asn Gly Arg Tyr Tyr Trp
                435                 440                 445

Gly Gly Gln Tyr Thr Trp Asp Met Ala Lys His Gly Thr Asp Asp Gly
                450                 455                 460

Val Val Trp Met Asn Trp Lys Gly Ser Trp Tyr Ser Met Arg Lys Met
465                 470                 475                 480
```

Ser Met Lys Ile Arg Pro Phe Phe Pro Gln Gln
            485             490

<210> SEQ ID NO 3
<211> LENGTH: 437
<212> TYPE: PRT
<213> ORGANISM: Homo sapiens

<400> SEQUENCE: 3

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
        50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
            115                 120                 125

His Asp Ser Ser Ile Arg Tyr Leu Gln Glu Ile Tyr Asn Ser Asn Asn
        130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
            195                 200                 205

Glu Ile Asp Gly Ser Gly Asn Gly Trp Thr Val Phe Gln Lys Arg Leu
        210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
            275                 280                 285

Ala Met Phe Lys Val Gly Pro Glu Ala Asp Lys Tyr Arg Leu Thr Tyr
        290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly

-continued

```
                355                 360                 365
His Leu Asn Gly Val Tyr Tyr Gln Gly Gly Thr Tyr Ser Lys Ala Ser
        370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Ala Gly Asp Val
            435

<210> SEQ ID NO 4
<211> LENGTH: 453
<212> TYPE: PRT
<213> ORGANISM: Homo sapiens

<400> SEQUENCE: 4

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285
```

| Ala | Met | Phe | Lys | Val | Gly | Pro | Glu | Ala | Asp | Lys | Tyr | Arg | Leu | Thr | Tyr |
| | 290 | | | | | 295 | | | | 300 | | | | | |

| Ala | Tyr | Phe | Ala | Gly | Gly | Asp | Ala | Gly | Asp | Ala | Phe | Asp | Gly | Phe | Asp |
| 305 | | | | | 310 | | | | | 315 | | | | | 320 |

| Phe | Gly | Asp | Asp | Pro | Ser | Asp | Lys | Phe | Phe | Thr | Ser | His | Asn | Gly | Met |
| | | | | 325 | | | | | 330 | | | | | 335 | |

| Gln | Phe | Ser | Thr | Trp | Asp | Asn | Asp | Asn | Asp | Lys | Phe | Glu | Gly | Asn | Cys |
| | | | 340 | | | | | 345 | | | | | 350 | | |

| Ala | Glu | Gln | Asp | Gly | Ser | Gly | Trp | Trp | Met | Asn | Lys | Cys | His | Ala | Gly |
| | | | 355 | | | | 360 | | | | | 365 | | | |

| His | Leu | Asn | Gly | Val | Tyr | Tyr | Gln | Gly | Gly | Thr | Tyr | Ser | Lys | Ala | Ser |
| | 370 | | | | | 375 | | | | 380 | | | | | |

| Thr | Pro | Asn | Gly | Tyr | Asp | Asn | Gly | Ile | Ile | Trp | Ala | Thr | Trp | Lys | Thr |
| 385 | | | | | 390 | | | | | 395 | | | | | 400 |

| Arg | Trp | Tyr | Ser | Met | Lys | Lys | Thr | Thr | Met | Lys | Ile | Ile | Pro | Phe | Asn |
| | | | | 405 | | | | | 410 | | | | | 415 | |

| Arg | Leu | Thr | Ile | Gly | Glu | Gly | Gln | Gln | His | His | Leu | Gly | Gly | Ala | Lys |
| | | | | 420 | | | | | 425 | | | | | 430 | |

| Gln | Val | Arg | Pro | Glu | His | Pro | Ala | Glu | Thr | Glu | Tyr | Asp | Ser | Leu | Tyr |
| | | | 435 | | | | | 440 | | | | | 445 | | |

| Pro | Glu | Asp | Leu | | | | | | | | | | | | |
| | 450 | | | | | | | | | | | | | | |

<210> SEQ ID NO 5
<211> LENGTH: 2598
<212> TYPE: DNA
<213> ORGANISM: Homo sapiens

<400> SEQUENCE: 5

```
atgttcagca tgaggatcgt gtgcctggtg ctgtccgtgg tgggcaccgc ctggaccgcc      60
gacagcggcg agggcgactt cctggccgag ggcggtggcg tgaggggccc cagggtggtg     120
gagaggcacc agagcgcctg caaggacagc gactggcccc tctgcagcga cgaggactgg     180
aactacaagt gccccagcgg ctgcaggatg aagggcctga tcgacgaggt gaaccaggac     240
ttcaccaaca ggatcaacaa gctgaagaac agcctgttcg agtaccagaa gaacaacaag     300
gacagccaca gcctgaccac caacatcatg gaaatcctga gggcgatttc tctagcgcc      360
aacaacaggg acaacaccta acagggtgtc cgaggaccc tgaggtccag gatcgaggtg      420
ctgaagagga aggtgatcga aggtgcag cacatccagc tgctgcagaa aacgtcagg        480
gcccagctgt cgacatgaa gaggctggaa gtggacatcg acatcaagat caggtcctgc     540
aggggcagct gcagccgggc tctggctaga gaggtggacc tgaaggacta cgaggaccag    600
cagaaacagc tggaacaggt gatcgccaag gacctgctgc ccagcaggga caggcagcac    660
ctgccctga tcaagatgaa gcccgtgccc gacctggtgc ccggcaactt caagagccag    720
ctgcagaaag tgccccccga gtggaaggcc ctgaccgaca tgccccagat gaggatggaa    780
ctggaaaggc aggcggcaa cgagatcacc aggggcggca gcaccagcta cggcaccggc   840
agcgagaccg agagcccag gaaccccagc agcgccggca gctggaactc cggcagcagc    900
ggcccaggct ccaccggcaa caggaacccc ggctccagcg caccggcgg gacagccacc    960
tggaagcccg gcagctccgg ccctggcagc accggctctt ggaacagcgg cagctctggc   1020
accgggagca cggcaaccaa gaacccaggc agccccaggc ctggctctac cgggacctgg   1080
aacccaggct cctccgagag gggctctgcc ggccactgga ccagcgagag cagcgtgagc   1140
```

| | |
|---|---:|
| ggcagcacag gccagtggca cagcgagtcc ggcagcttca ggcccgacag ccccggcagc | 1200 |
| ggcaacgcca ggcccaacaa ccccgactgg ggcaccttcg aggaagtgag cggcaacgtg | 1260 |
| agccccggca ccaggcggga gtaccacacc gagaagctgg tgaccagcaa gggcgacaaa | 1320 |
| gagctgagga ccggcaaaga aaaggtgacc agcggctcta ccaccaccac caggcggagc | 1380 |
| tgcagcaaga ccgtgaccaa gacagtgatc ggccccgacg ccacaaaga ggtgaccaaa | 1440 |
| gaagtcgtga ccagcgagga cggcagcgac tgccccgagg ccatggacct gggcaccctg | 1500 |
| agcggcatcg gcaccctgga cggcttcagg cacaggcacc ccgacgaggc cgccttcttc | 1560 |
| gacaccgcca gcaccggcaa gaccttcccc ggcttcttca gccccatgct gggcgagttc | 1620 |
| gtgtccgaga ccgagtcccg cggcagcgag agcggcatct tcaccaacac caaagagtcc | 1680 |
| agcagccacc atcccggcat cgctgagttc cccagcaggg gcaagagcag ctcctacagc | 1740 |
| aagcagttca ccagcagcac cagctacaac aggggcgaca gcaccttcga gagcaagagc | 1800 |
| tacaagatgg ccgacgaggc cggctctgag gccgaccacg agggcaccca cagcaccaag | 1860 |
| agggggccacg ccaagagcag gcccgtgagg gactgcgacg acgtgctgca gacccacccc | 1920 |
| agcggcaccc agtctggcat cttcaacatc aagctgcccg gcagcagcaa gatcttcagc | 1980 |
| gtgtactgcg accaggaaac cagcctgggc ggctggctgc tgatccagca gaggatggac | 2040 |
| ggcagcctga acttcaacag gacctggcag gactacaaga ggggcttcgg ctccctgaac | 2100 |
| gacgagggc agggcgagtt ctggctgggc aacgactacc tgcacctgct gacccagagg | 2160 |
| ggatctgtcc tgagggtcga gctggaagat tgggccggca cgaggcctac gccgagtac | 2220 |
| cacttcagag tgggcagcga ggccgagggc tacgctctgc aggtgtccag ctacgagggc | 2280 |
| acagccggcg acgccctgat cgagggcagc gtggaagagg gcgccgagta caccagccac | 2340 |
| aacaacatgc agttctccac cttcgacagg gacgccgacc agtgggagga aaactgcgcc | 2400 |
| gaggtgtacg gcggagggtg gtggtacaac aactgccagg ccgccaacct gaacggcatc | 2460 |
| tactacccag gcggcagcta cgaccccagg aacaacagcc cctacgagat cgagaacggc | 2520 |
| gtggtgtggg tgtccttcag aggcgccgac tacagcctga gggccgtgag gatgaagatc | 2580 |
| aggccccctgg tgacccag | 2598 |

<210> SEQ ID NO 6
<211> LENGTH: 1473
<212> TYPE: DNA
<213> ORGANISM: Homo sapiens

<400> SEQUENCE: 6

| | |
|---|---:|
| atgaagagga tggtgtcctg gtccttccac aagctgaaaa caatgaagca cctgctcctc | 60 |
| ctcctcctct gcgtgttcct ggtgaagagc cagggcgtga cgacaacga agagggcttc | 120 |
| ttcagcgcca gaggacaccg ccccctggac aagaagagag aagaggcccc cagcctgaga | 180 |
| cccgccccac cccaatcag cggcggaggg tacagagcca ggcccgccaa ggctgccgcc | 240 |
| acccagaaga aggtcgaacg gaaggctccc gacgccggag gatgcctgca cgccgacccc | 300 |
| gacctgggcg tgctgtgccc caccggctgc cagctgcagg aagctctgct ccagcaggaa | 360 |
| aggcccatca gaaacagcgt ggacgagctg aacaacaacg tggaggccgt gagccagacc | 420 |
| agcagcagca gcttccagta catgtacctg ctgaaggacc tgtggcagaa gaggcagaag | 480 |
| caggtcaaag acaacgagaa cgtggtgaac gagtacagca gcgagctgga gaagcaccag | 540 |
| ctgtacatcg acgagaccgt gaacagcaat atcccaacca acctgagggt gctgagaagc | 600 |
| atcctggaga acctgaggtc caagatccag aagctggaga gcgacgtcag cgcccagatg | 660 |

```
gagtactgca ggacccctg caccgtgtcc tgcaacatcc cagtggtgtc cggcaaggaa      720
tgcgaggaaa tcatcaggaa gggcggcgag accagcgaga tgtacctgat ccagcccgac      780
agcagcgtga agccctacag ggtgtactgc gacatgaaca ccgagaatgg gggctggacc      840
gtcatccaga caggcagga cggcagcgtg gacttcggca ggaagtggga cccctacaag      900
cagggcttcg gcaacgtggc caccaacacc gacggcaaga actactgcgg cctgcctggc      960
gagtattggc tgggaaacga caagatcagc cagctgacca ggatgggccc aaccgagctg     1020
ctgatcgaga tggaggactg aagggcgac aaggtgaaag cccactacgg cggcttcacc     1080
gtgcagaacg aggccaacaa gtaccagatc agcgtgaaca agtacagggg caccgccggc     1140
aacgccctga tggacggcgc ctcccagctg atgggcgaga caggaccat gaccatccac     1200 aacggcatgt tcttcagcac ctacgacagg acaacgacg gctggctgac cagcgacccc     1260
agaaagcagt gcagcaagga agatggcgga ggatggtggt acaacaggtg ccacgccgcc     1320
aaccccaacg gcaggtacta ctggggcgga cagtacacct gggacatggc caagcacggc     1380
accgacgacg gcgtggtgtg gatgaactgg aagggggtcct ggtacagcat gaggaagatg     1440
agcatgaaga tcaggccatt ctttccacag cag                                  1473

<210> SEQ ID NO 7
<211> LENGTH: 1311
<212> TYPE: DNA
<213> ORGANISM: Homo sapiens

<400> SEQUENCE: 7
atgagctggt ccctgcaccc caggaacctg atcctgtact tctacgccct gctgttcctg       60
agcagcacat gcgtcgccta tgtggctacc agggacaact gctgcatcct ggacgagagg      120
ttcggcagct actgccccac cacctgcggc atcgccgact ttctgagcac ctaccagacc      180
aaggtggaca ggaccctgca gagcctggag gacatcctgc accaggtgga gaacaagacc      240
agcgaggtga agcagctgat caaggccatc cagctgacct acaaccccga cgagagcagc      300
aagcccaaca tgatcgacgc cgccaccctg aagagcagga agatgctgga ggaaatcatg      360
aagtacgagg ccagcatcct gacccacgac agcagcatca gataccctgca ggaaatctac      420 aacagcaaca accagaagat cgtcaacctg aaggaaaagg tcgcccagct ggaagcccag      480
tgccaggaac cctgcaagga caccgtgcag atccacgaca tcaccggcaa ggactgccag      540
gacatcgcca caagggcgc caagcagagc ggcctgtact tcatcaagcc cctgaaggcc      600
aaccagcagt tcctggtgta ctgcgagatc gacggcagcg gcaacggctg gaccgtgttc      660
cagaagaggc tggacggcag cgtggacttc aagaagaact ggattcagta caaggaaggc      720
ttcggccacc tgagccccac cggcaccacc gagttctggc tgggcaacga aaagatccac      780
ctgatcagca cccagagcgc catcccatac gccctgaggg tggagctgga ggactggaac      840
ggcaggacca gcaccgccga ctacgccatg ttcaaagtgg acccgaggc cgacaagtac      900 aggctgacct acgcctactt tgccggaggg gacgctggcg acgccttcga cggcttcgac      960
ttcggcgacg accccagcga caagttcttc accagccaca cggcatgca gttcagcacc     1020 tgggacaaca caacgacaa gttcgagggc aactgcgccg agcaggacgg ctccgggtgg     1080
tggatgaaca agtgccacgc cgggcacctg aacggcgtgt actaccaggg cggcacctac     1140
agcaaggcca gcaccccaa cggctacgac aacggcatca tctgggccac ctggaaaacc     1200
aggtggtaca gcatgaaaaa aaccaccatg aagatcatcc cattcaacag actgaccatc     1260
```

```
ggcgagggcc agcagcacca cctgggcgga gccaagcagg ctggcgacgt g          1311

<210> SEQ ID NO 8
<211> LENGTH: 1359
<212> TYPE: DNA
<213> ORGANISM: Homo sapiens

<400> SEQUENCE: 8
atgagctggt ccctgcaccc caggaacctg atcctgtact tctacgccct gctgttcctg     60
agcagcacat gcgtcgccta tgtggctacc agggacaact gctgcatcct ggacgagagg    120
ttcggcagct actgccccac cacctgcggc atcgccgact ttctgagcac ctaccagacc    180
aaggtggaca aggacctgca gagcctggag gacatcctgc accaggtgga gaacaagacc    240
agcgaggtga agcagctgat caaggccatc cagctgacct acaaccccga cgagagcagc    300
aagcccaaca tgatcgacgc cgccaccctg aagagcagga gatgctgga ggaaatcatg     360 aagtacgagg ccagcatcct gacccacgac agcagcatca gatacctgca ggaaatctac    420
aacagcaaca accagaagat cgtcaacctg aaggaaaagg tcgcccagct ggaagcccag    480
tgccaggaac cctgcaagga caccgtgcag atccacgaca tcaccggcaa ggactgccag    540
gacatcgcca caagggcgc caagcagagc ggcctgtact tcatcaagcc cctgaaggcc     600
aaccagcagt tcctggtgta ctgcgagatc gacggcagcg gcaacggctg gaccgtgttc    660
cagaagaggc tggacggcag cgtggacttc aagaagaact ggattcagta caaggaaggc    720
ttcggccacc tgagccccac cggcaccacc gagttctggc tgggcaacga gaagatccac    780
ctgatcagca cccagagcgc catcccatac gccctgaggg tggagctgga ggactggaac    840
ggcaggacca gcaccgccga ctacgccatg ttcaaagtgg acccgaggc cgacaagtac     900 aggctgacct acgcctactt tgccggaggg gacgctggcg acgccttcga cggcttcgac    960
ttcggcgacg accccagcga caagttcttc accagccaca acggcatgca gttcagcacc   1020
tgggacaacg acaacgacaa gttcgaggggc aactgcgccg agcaggacgg ctccgggtgg   1080
tggatgaaca agtgccacgc cgggcacctg aacggcgtgt actaccaggg cggcacctac   1140
agcaaggcca gcacccccaa cggctacgac aacggcatca tctgggccac ctggaaaacc   1200
aggtggtaca gcatgaaaaa aaccaccatg aagatcatcc cattcaacag actgaccatc   1260
ggcgagggcc agcagcacca cctgggcgga gccaagcagg tgcggccaga gcacccgcc    1320 gagacagagt acgacagcct gtaccccgag gacgacctg                          1359
```